United States Patent [19]

Higley et al.

[11] Patent Number: 5,723,441
[45] Date of Patent: Mar. 3, 1998

[54] METHOD OF TREATING RENAL DISEASE BY ADMINISTERING IGF-I AND IGFBP-3

[75] Inventors: Howard R. Higley, Mountain View; Christopher A. Maack, El Cerrito, both of Calif.

[73] Assignee: Celtrix Pharmaceuticals, Inc., Santa Clara, Calif.

[21] Appl. No.: 521,907

[22] Filed: Aug. 31, 1995

Related U.S. Application Data

[63] Continuation of Ser. No. 353,141, Dec. 9, 1994, abandoned, which is a continuation of Ser. No. 152,862, Nov. 15, 1993, abandoned.

[51] Int. Cl.$^6$ .......................... A61K 38/00; A61K 38/28; A61K 38/27
[52] U.S. Cl. .................... 514/12; 514/8; 514/21
[58] Field of Search .................... 514/12, 21, 8

[56] References Cited

U.S. PATENT DOCUMENTS

| | | | |
|---|---|---|---|
| 3,773,919 | 11/1973 | Boswell et al. | 424/486 |
| 5,106,832 | 4/1992 | Froesch et al. | 514/3 |
| 5,273,961 | 12/1993 | Clark | 514/8 |

FOREIGN PATENT DOCUMENTS

| | | |
|---|---|---|
| 0128733 | 12/1984 | European Pat. Off. |
| 0327503 | 8/1989 | European Pat. Off. |

OTHER PUBLICATIONS

Guler et al., "Recombinant human insulin-like growth factor I stimulates growth and has distinct effects on organ size in hypophysectomized rats," (1988) Proc. Nat'l Acad. Sci. USA 85:488–4893.

Rabkin et al., "Insulin-like growth factor-1 (IGF-1) enhances recovery from acute renal failure (ARF) induced by ischemia" *J. Am. Soc. Nephrol.* (1992) 3:713.

Andersson et al., "IGF-1 immunoreactivity is expressed by regenerating renal tubular cells after ischaemic injury in the rat" *Acta Physiologica Scandinavica* (1988) 132:453–457.

Sommer et al., in "Modern Concepts of Insulin like Growth Factors" pub 1991, Elsevier Pub. Co. pp. 715–728.

Blum et al., "Plasma IGFBP-3 levels as clinical indicators" *Modern Concepts in Insulin-Like Growth Factors* (1991) Spencer, E. M., ed., Elsevier, New York, pp. 381–393.

Rinderknecht et al., "Polypeptides with nonsuppressible insulin-like and cell-growth promoting activities in human serum: Isolation, chemical characterization, and some biological properties of forms I and II" *Proc. Natl. Acad. Sci. USA* (1976) 73(7):2365–2369.

Baxter et al., "Growth hormone-dependent insulin-like growth (IGF) binding protein from human plasma differs from other human IGF binding proteins" *Biochem. Biophys. Res. Comm.* (1986) 139(3):1256–1261.

Sommer et al., "Molecular genetics and actions of recombinant insulin-like growth factor binding protein-3" *Modern Concepts In Insulin-Like Growth Factors* (1991) Spencer, E.M., Elsevier, New York, pp. 715–728.

Miller et al., "Effects of growth hormone and IGF-I on renal function in rats with normal and reduced renal mass" *Am. J. Physiol.* (1990) 259:F747–F751.

Miller et al., "Insulin-like growth factor I accelerates recovery from ischemic acute tubular necrosis in the rat" *Proc. Natl. Acad. Sci. USA* (1992) 89:11876–11880.

Ritz et al., "Influence of growth hormone and insulin-like growth factor-I on kidney function and kidney growth" *Pediatr. Nephrol.* (1991)5:509–512.

Blum et al., "Growth hormone resistance and inhibition of somatomedin activity by excess of insulin-like growth factor binding protein in uraemia" *Pediatr. Nephrol.* (1991) 5:539–544.

Mulroney et al., "Altered expression of insulin-like growth factor-I (IGF-I) and IGF receptor genes after unilateral nephrectomy in immature rats" *Endocrinol.* (1992) 130(1):249–256.

Flyvbjerg et al., "Kidney IGF-I accumulation occurs in four different conditions with rapid initial kidney growth in rats" *Modern Concepts In Insulin-Like Growth Factors* (1991) Spencer, E.M., ed., Elsevier, New York, pp. 207–217.

Guyda, H. "Concepts of IGF physiology" *Modern Concepts In Insulin-Like Growth Factors* (1991) Spencer, E.M., ed., Elsevier, New York, pp. 99–109.

Chin et al., "Renal growth horome receptor gene expression: relationship to renal insulin-like growth factor system" *Endocrinol.* (1992) 131(6):3061–3066.

Bach et al., "Diabetes-related renal growth and IGF-I accumulation in castrated rats" *Diabetes Res. Clin. Pract.* (1991) 14:15–20.

Martin et al., "IGF-I and its variant, des-(1–3)IGF-I, enhance growth in rats with reduced renal mass" *Am. J. Physiol.* (1991) 261:F626–F633.

Guler et al., "Effects of recombinant insulin-growth factor I on insulin secretion and renal function in normal human subjects" *Proc. Natl. Acad. Sci. USA* (1989) 86:2868–2872.

Guler et al., "Short-term metabolic effects of recombinant human insulin-like growth factor I in healthy adults" *N. Engl. J. Med.* (1987) 317(3):137–140.

Sidmon et al., "Controlled release of macromolecules and pharmaceuticals from synthetic polypeptides based on glutamic acid" *Biopolymers* (1983) 22(1):547–556.

(List continued on next page.)

*Primary Examiner*—Cecilia J. Tsano
*Assistant Examiner*—P. L. Touzeau
*Attorney, Agent, or Firm*—Morrison & Foerster

[57] ABSTRACT

Treatment with IGF/IGFBP-3 complex increases renal tubular mass and potentiates and/or stimulates kidney function in subjects suffering from acute and chronic renal failure or insufficiency resulting from such disorders as glomerulonephritis, glomerulosclerosis, interstitial nephritis, acute tubular necrosis due to ischemia and drug-induced toxicity, diabetic and autoimmune nephropathies and renal dysfunction due to acute and chronic rejection episodes in post-transplantation patients.

18 Claims, 1 Drawing Sheet

OTHER PUBLICATIONS

Langer et al., "Biocompatibility of polymeric delivery systems for macromolecules" *J. Biomed. Res.* (1981) 15:267–277.

Hirschberg et al., "The effects of insulin–like growth factor I on renal hemodynamics" *Modern Concepts In Insulin–Like Growth Factors* (1991) Spencer, E. M., ed., Elsevier, New York, pp. 199–206.

Ho et al, "The antinatriuretic action of biosynthetic human growth hormone in man involves activation of the renin–angiotensin system" *Metabolism* (1990) 39(2):133–137.

Kanda et al., "Anti–epidermal growth factor antibody inhibits compensatory renal hyperplasia but not hypertrophy after unilateral nephrectomy in mice" *Biochem. Biophys. Res. Comm.* (1992) 187(2):1015–1021.

Mehls et al., "Growth hormone in renal transplantation—the mode of action, animal studies, and clinical use" *J. Am. Soc. Nephrol.* (1992) 2:S284–S289.

Mehls et al., "Growth hormone and insulin–like growth factor in chronic renal failure–pathophysiology and rationale for growth hormone treatment" *Acta. Paediatr. Scand. (Suppl).* (1990) 370:28–34.

Rogers et al., "Growth hormone stimulates IGF I gene expression in isolated rat renal collecting duct " *Am. Physiol. Soc.* (1990) pp. F474–F479.

METHOD OF TREATING RENAL DISEASE BY ADMINISTERING IGF-I AND IGFBP-3

This application is a continuation of application Ser. No. 08/353,141 filed Dec. 9, 1994 now abandoned, which is a continuation of application Ser. No. 08/152,862, filed Nov. 15, 1993, now abandoned.

TECHNICAL FIELD

This invention relates to the treatment of kidney diseases. The method comprises administering a complex comprising insulin-like growth factor (IGF) and an insulin-like growth factor binding protein (IGFBP).

BACKGROUND ART

Growth factors are polypeptides which stimulate a wide variety of biological responses (e.g., DNA synthesis, cell division, expression of specific genes, etc.) in a defined population of target cells. A variety of growth factors have been identified including transforming growth factor-β1 (TGF-β1), TGF-β2, TGF-β3, epidermal growth factor (EGF), platelet-derived growth factor (PDGF), fibroblast growth factor (FGF), insulin-like growth factor-I (IGF-I), and IGF-II.

IGF-I and IGF-II are polypeptides related in sequence and structure, with each molecule having a molecular weight of approximately 7500 daltons. IGF-I acts as the mediator of the effects of growth hormone (GH) and thus is the primary mediator of growth after birth. In contrast, IGF-II is believed to play a major role in fetal growth. IGF-I has also been implicated in the actions of various other growth factors, since treatment of cells with such growth factors leads to increased production of IGF-I. Both IGF-I and IGF-II have insulin-like activities (hence the name), and are mitogenic for the cells in reproductive tissue, muscle, skeletal tissue and a wide variety of other tissues.

Unlike most growth factors, the IGFs are present in substantial quantity in the circulation, but only a very small fraction of this IGF is found in the free form in the circulation or in other body fluids. The overwhelming majority of IGF circulates as part of a non-covalently associated ternary complex composed of IGF-I or IGF-II, an IGF specific binding protein termed IGFBP-3, and a large protein termed the acid labile subunit (ALS). This complex is composed of equimolar amounts of each of the three components. The ALS has no direct IGF binding activity and is thought to only be able to bind a preformed IGF-I/IGFBP-3 complex. The ternary complex of IGF+IGFBP-3+ALS has a molecular weight of approximately 150,000 daltons, and it has been suggested that the function of such a unit in the circulation "may be regarded as a reservoir and a buffer for IGF-I and IGF-II preventing rapid changes of free IGF." See Blum, W. F., et al. (1991), Plasma IGFBP-3 levels as clinical indicators, In: Modern Concepts in Insulin-Like Growth Factors (E. M. Spencer), pages 381–393.

Nearly all of the IGF-I or IGF-II and IGFBP-3 in the circulation are complexed with each other, so there is very little free IGF or IGFBP-3 detectable. High levels of free IGF in plasma must be avoided as they would lead to serious hypoglycemia due to IGF's insulin-like effects on glucose transport into tissues. In contrast to the IGFs and IGFBP-3, there is a substantial pool of free ALS present in plasma which is available for ternary complex formation with exogenously administered IGF-I/IGFBP-3 complex.

Although IGFBP-3 is the most abundant IGF binding protein in the circulation, at least five other distinct IGF binding proteins (IGFBPs) have been identified in various tissues and body fluids. Although these proteins bind IGFs, they each have distinct amino acid sequences, and are not merely processed forms of a common precursor. Unlike IGFBP-3, the other IGFBPs that are present in the circulation are not saturated with IGFs and constitute the majority of the available soluble IGF binding sites in plasma. None of the IGF binding proteins other than IGFBP-3 can form the 150 kd circulating ternary complex.

IGF-I and IGFBP-3 may be purified from natural sources or produced from recombinant sources. For instance, IGF-I has been purified from human serum for a number of years. See, Rinderknecht, et al. (1976) Proc. Natl. Acad. Sci. (USA) 73:2365–2369. Recombinant IGF-I processes are shown in EPA 0,128,733, published in December of 1984. IGFBP-3 may be purified from natural sources using processes such as those discussed in Baxter, et al. (1986) Biochem. Biophys. Res. Comm. 139:1256–1261. IGFBP-3 may be synthetically produced from recombinant sources as discussed in Sommer, et al. (1991), in MODERN CONCEPTS OF INSULIN-LIKE GROWTH FACTORS. (E. M. Spencer, ed., Elsevier, N.Y.), pp. 715–728.

IGF-I may be measured in blood serum to diagnose abnormal growth-related conditions, e.g. pituitary gigantism, acromegaly, dwarfism, various growth hormone deficiencies, etc. Although IGF-I is produced in many tissues, most circulating IGF-I is believed to be synthesized in the liver.

Many of the important elements of the IGF system are found in the kidney. The kidney functions in the maintenance of fluid and electrolyte balance, pH control, and the filtration and clearance of metabolic waste products while resorbing critical serum proteins and returning them to the bloodstream. In addition, the kidney produces several critical vaso- and hemato-regulatory substances in response to variations in vascular tone and blood cell mass.. These activities are accomplished at the level of the nephron and its associated renal vascular plexus. The anatomical compartmentalization of the kidney permits the filtration and resorption functions performed by the glomerular capillary tuft and capsule and the convoluted segments of the epithelial tubules to take place in the outer cortical portion of the organ while the osmoregulatory and urinary concentration functions take place in the 'hair-pin loop' straight segments of the epithelial tubules and collecting ducts in the inner medulla. See, generally, Guyton, A., TEXTBOOK OF MEDICAL PHYSIOLOGY, the most recent edition.

Assessment of the efficacy and coordination of these diverse renal functions and the impact of various regulatory molecules on these functions has been accomplished by use of a variety of techniques in both humans and experimental animals. The concentration of the normally cleared catabolic end products, creatinine and urea (typically calculated as BUN) in the blood are often used as indirect measurements of renal function. Infusion of various artificial non-metabolized polysaccharides such as inulin and PAH into the bloodstream with periodic blood and urine sampling to determine their relative concentrations also permits calculation of both glomerular filtration rate (GFR) and renal plasma flow (RPF). Guyton, A., ibid. Experimental reduction of renal mass such as in unilateral nephrectomy models or compromise of renal integrity induced by renal artery ligation (Miller, et al. (1990) Amer. J. Physiol. 259:F747–751; Miller, et al. (1992) PNAS 89:11876–11880), as well as various human disease states (Ritz, et al. (1991) Pediatr. Nephrol. 5:509–512; Blum, W., et al. (1991) Pediatr. Nephrol. 5:539–544), typically result in decreases in GFR and RPF and increases in serum creatinine and BUN of varying severity. Proteinuria and changes in urinary electrolytes are also indicators of failure of the normal tubular resorption in the damaged kidney. Miller, et al., (1990) *Amer. J. Physiol.* 259:F747–751; Miller, et al., (1992) *PNAS* 89:11876–11880; Ritz, et al., (1991) *Pediatr. Nephrol.* 5:509–512; Blum, et al., (1991) *Pediatr. Nephrol.* 5:539–544.

Intrinsic compensatory and repair mechanisms can limit the morbidity and mortality associated with partial kidney damage. The remaining renal tissues undergo hypertrophic and hyperplastic changes that can restore large amounts of both renal mass and function. Key mediators of the repair responses are thought to be growth hormone and the insulin-like growth factors. Mulroney, et al. (1992) *Endocrinology* 130(1):249–256; Flyvbjerg, et al. In: MODERN CONCEPTS OF INSULIN-LIKE GROWTH FACTORS (ed. by E. Spencer), 1991, pp. 207–217. These polypeptides have been shown to have receptors on and mediate general anabolic effects in virtually all cells and tissues of the body. (Guyda, H., In: MODERN CONCEPTS OF INSULIN-LIKE GROWTH FACTORS (ed. by E. Spencer) 1991, pp. 97–109); but unique renotrophic effects have been described.

It has long been recognized that individuals with hypopituitarism or animals after hypophysectomy have a decreased GFR, while acromegalics have an increased GFR and renal size and weight. Ritz, et al. (1991) supra. Administration of GH to humans or experimental animals causes an increase in renal function gradually, over a time course that suggests the induction of an additional mediator, likely IGF. Miller, et al. (1990) supra.

In the kidney, mRNAs for IGF-I, the IGF-I receptor and the GH receptor have been demonstrated in various segments of the tubular epithelium. Both IGF message and immunoreactivity increase during kidney development and in the compensatory growth response seen after partial nephrectomy. Mulroney, et al. (1992) supra; Chin et al. (1992) *Endocrinology* 131(6):3061–3066. IGF-I content of the kidney also increases in the pathologic renal enlargement seen in diabetes and potassium deficiency. Flyvbjerg, et al. (1991) supra; Bach, et al. (1991) *Diabetes Res. Clin. Pract.* 14:15–20.

Infusion of IGF-I or its analogs into rats that had been partially nephrectomized or had been subjected to an acute ischemic renal insult resulted in either accelerated restoration of renal mass or renal function as well as an overall reduction in body weight decline and mortality. Miller, et al. (1992), supra; Martin, et al. (1991) *Amer. J. Physiol.* 261:F626–633. The pharmacologic effects of IGF-I in these models were comparable or superior to those seen with treatment with either GH or EGF.

It has also been observed that the growth retardation seen in children with chronic renal failure and the general catabolism seen in end-stage renal failure and dialysis is associated with decreased serum levels of IGF-I bioactivity rather than insufficient GH. Blum, et al. (1991) supra. Although treatment of these children with GH results in some increase in somatic growth rate, their renal disease is not improved and thus is said to be growth hormone "resistant". The presence of excessive levels of IGF binding proteins in uremic patients may impair renal repair mechanisms.

Therefore, it can be seen that there is a need in the art to supply therapeutics that will modulate or repair kidney structure and restore kidney function which is not performed by GH alone. Infusion of recombinant IGF-I into normal human subjects has been reported to increase GFR (Guler, et al. (1989) *PNAS* 86:2868–2872) and has been proposed as a therapeutic strategy for the treatment of renal diseases. Froesch, et al. U.S. Pat. No. 5,106,832 (issued on Apr. 21, 1992). However, the use of IGF-I alone in these indications may have at least one severe limitation, the generation of hypoglycemia on bolus administration of high doses of IGF-I.

Indeed, although no limiting hypoglycemia was seen in normal subjects or in mini-poodles treated with 20 µg/kg IGF-I for the assessment of renal function (Froesch, et al., ibid.), intravenous administration of 100 µg/kg IGF-I did produce acute hypoglycemic episodes in most subjects in a previous test of IGF-I action. Guler, et al. (1987) *N. Engl. J. Med.* 317:137–140. Although this side effect may be avoided in part by slow infusion of IGF-I or by multiple low dose subcutaneous treatments with IGF-I, these methods may not deliver the supraphysiologic levels needed without also causing hypoglycemia.

DISCLOSURE OF INVENTION

In view of this art, the present invention represents an unexpected finding that treatment with IGF-I/IGFBP-3 complex can increase renal mass and alter kidney function. This method can be useful in the treatment of individuals suffering from acute or chronic renal failure or insufficiency resulting from such disorders as glomerulonephritis, glomerulosclerosis, interstitial nephritis, acute tubular necrosis due to ischemia or drug induced toxicity, diabetic or autoimmune nephropathies or renal dysfunction due to acute or chronic rejection episodes in post-transplantation patients.

Treatment with IGF IGFBP-3 complex in a defined ratio of growth factor:binding protein is a therapy superior to that achieved by treatment with IGF alone, IGF in combination with GH, IGF complexed with other binding proteins and the IGFBP-3 complex at other than the optimum ratio of growth factor:binding protein of 1:1.

In accordance with one embodiment of the present invention, there is provided a method for the treatment of renal disorders, wherein the method comprises administering to an individual a complex comprising an insulin-like growth factor (IGF) and insulin-like growth factor binding protein-3 (IGFBP-3) in an amount sufficient to treat kidney disease.

In accordance with another embodiment of the present invention, the IGF used in the complex is provided as IGF-I. In a further embodiment, IGF and IGFBP are present in equimolar amounts. In still another embodiment, both IGF and IGFBP-3 are non-glycosylated human proteins obtained from recombinant sources.

In accordance with another embodiment of the present invention, the complex of IGF and IGFBP-3 is administered by subcutaneous injection.

In yet another embodiment, the method of the present invention provides treatment of an renal disorder with a complex of IGF and IGFBP-3.

In another embodiment, the individual to whom the complex is administered is a mammal.

In a further embodiment, the amount of IGF/IGFBP-3 complex administered is at least about 0.05 to 10 mg/kg/day.

While not wishing to be bound by any particular theory, the inventors propose that the administration of IGF in combination with IGFBP-3 results in the gradual release of free IGF in supraphysiologic levels without causing hypoglycemia. This can occur either before or after the circulating IGF/IGFBP-3 complex is taken up into the kidneys. Treatment with the IGF-I/IGFBP-3 complex increases renal mass and potentiates or stimulates kidney function.

MODES FOR CARRYING OUT THE INVENTION

Figure 1:
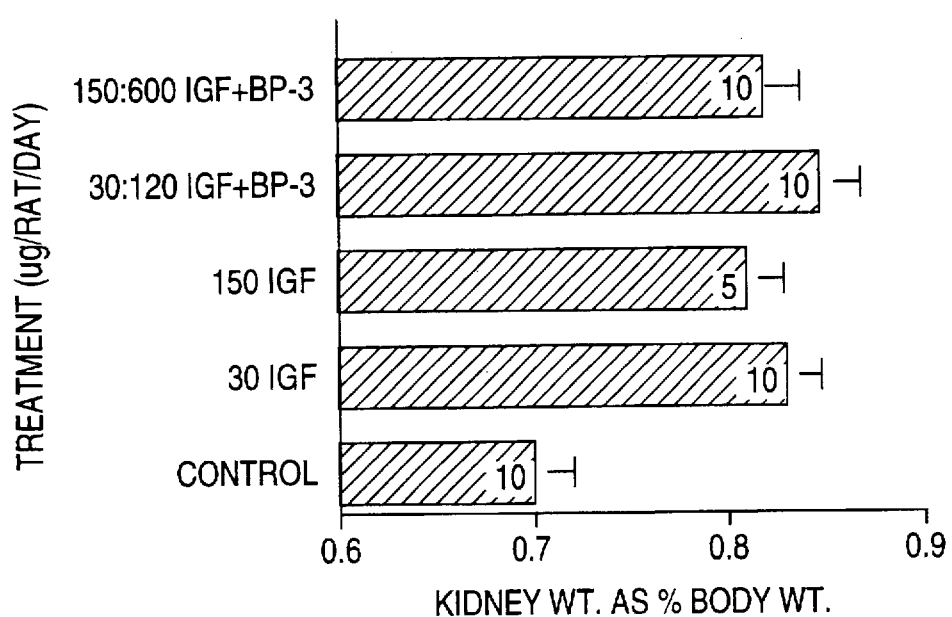
FIG. 1 shows the effect of treatment with doses of IGF-I/IGFBP-3 complex or equivalent doses of IGF-I alone on kidney weight as a percentage of total body weight.

Definitions:

As used herein, "renal disorders" are defined as renal insufficiency associated with a previous history of acute or chronic renal failure which optionally may require dialysis; conditions such as glomerulonephritis, glomerulosclerosis, interstitial nephritis, acute tubular necrosis due to ischemia; renal dysfunction associated with diabetes or autoimmune nephropathies; adverse reactions to nephrotoxic drugs or renotoxic immunosuppressives administered for organ transplantation, acute rejection episodes in post-kidney transplantation patients; and physical findings such as uremia, proteinuria, anuria.

"Subjects" are defined as humans and mammalian farm animals, sport animals and pets. Farm animals include, but are not limited to, cows, hogs and sheep. Sport animals include, but are not limited to, dogs and horses. The category pets includes, but is not limited to, cats and dogs.

"Insulin-like growth factor (IGF)" comprises a family of factors, including but not limited to IGF-I and IGF-II. IGF is a polypeptide having a molecular weight of about 7500 daltons. IGF may be obtained from natural sources or prepared by recombinant or chemical means.

"Insulin-like growth factor binding proteins (IGFBP)" comprises a family of binding proteins, including but not limited to IGFBP-1, IGFBP-2, IGFBP-3, IGFBP-4, IGFBP-5 and IGFBP-6. IGFBP may be obtained from natural sources or prepared by recombinant or chemical means. At least one form of IGFBP (for example, IGFBP-3) complexes with IGF and with a third molecule known as ALS.

A "therapeutic composition" as used herein is defined as comprising IGF complexed with its binding protein IGFBP-3. The therapeutic composition may also contain excipients such as water, minerals and carriers such as proteins.

DESCRIPTION OF THE INVENTION

The method of the present invention contemplates treating and alleviating conditions in subjects suffering from renal insufficiency or failure by administering IGF and IGFBP-3.

Nearly all IGF-I or IGF-II complex with IGFBP-3 and IGF/IGFBP-3 normally circulate in the form of a complex in humans and other mammals. This complex associates with a third protein (ALS), which is present in excess over the concentration of IGF-I and IGFBP-3. Therefore, ALS is found both associated with the IGF/IGFBP-3 complex and in the free form. The resultant ternary complex has a size of about 150 kd. Administration of IGF and IGFBP-3, either from natural or recombinant sources, as a preformed complex results in the formation of the normal ternary complex with the excess ALS. This type of treatment appears to produce a long term increase in the level of circulating IGF, which is gradually released from the ternary complex. This mode of administration avoids the detrimental side effects associated with administration of free IGF-I, e.g., hypoglycemia, suppression of growth hormone and ALS production, and release of endogenous IGF-II since administered exogenous free IGF-I replaces endogenous IGF-II in normally circulating IGF-II/IGFBP-3 complexes. Moreover, a greater total dosage of IGF-I can be safely delivered when complexed to its binding protein IGFBP-3 because of the protection provided by the complex from the generation of injurious hypoglycemia. Although this side effect of free IGF-I administration may be avoided in part by slow infusion or by multiple low dose treatments with IGF-I, slower infusion may not produce the supraphysiologic IGF levels required. Thus, treatment with the IGF-I/IGFBP-3 complex is more convenient, less expensive and more likely to be effective and to meet with higher patient compliance.

The formulation, method of administration and dosage will depend upon the disorder to be treated, and the medical history of the patient. These factors are readily determined in the course of therapy. Suitable patients with renal disorders can be identified by medical history, physical findings and laboratory tests. The medical history may reveal such facts as acute or chronic renal failure, resulting from diabetes, ischemia, drug induced toxicity, post-transplantation rejection with or without the need for dialysis; glomerulonephritis; glomerulosclerosis; interstitial nephritis; and acute tubular necrosis. Patients may have physical findings such as anuria, lethargy, coma and decreased general growth rate. Indicative laboratory results include increased plasma levels of creatinine, urea and uric acid (BUN), proteinuria, decreased GFR, RPF and renal size as determined by urogram, altered acid/base balance and changes in urine specific gravity.

In accordance with the method of the present invention, the formulation comprises a IGF and IGFBP-3. Preferably, the IGF is IGF-I, although IGF-II may be useful. Because IGF and IGFBP-3 naturally complex in a 1:1 molar ratio, a composition of equimolar amounts of IGF and IGFBP-3 is preferred. However, the product can be formulated with IGF:IGFBP-3 molar ratios ranging from 0.5 to 1.5. More preferably, the molar ratio is 0.9 to 1.3; and most preferably, the product is formulated with approximately a 1:1 molar ratio.

In accordance with the method of the present invention, the IGF and IGFBP-3 are human proteins obtained from natural or recombinant sources. Most preferably, IGF and IGFBP-3 are human IGF-I and IGFBP-3 made by recombinant means and designated rhIGF-I and rhIGFBP-3, respectively. rhIGFBP-3 may be in glycosylated or non-glycosylated form. $E.\ coli$ is a source of the non-glycosylated IGFBP-3. Glycosylated IGFBP-3 may be obtained from Chinese hamster ovary (CHO) cells.

The method of the present invention provides for formulating the combination in modes which are readily apparent to those skilled in the art. Preferably, the IGF and IGFBP-3 are complexed prior to administration to the treated individual. Preferably, the complex is formed by mixing approximately equimolar amounts of IGF-I and IGFBP-3 dissolved in physiologically compatible carriers such as normal saline solution or phosphate buffer saline solution. Most preferably, a concentrated solution of rhIGF-I and a concentrated solution of rhIGFBP-3 are mixed together for a sufficient time to form an equimolar complex.

Depending on the mode of administration, compositions of the complex may be in the form of solid, semi-solid or liquid dosage preparations, such as for example, tablets, pills, powders, capsules, liquids, suspensions or the like. Physiologically compatible carriers include intravenous solutions, such as normal saline, serum albumin, 5% dextrose, plasma preparations, and other protein-containing solutions. The preferred carrier for parenteral administration of the complex is a sterile, isotonic aqueous solution, such as normal saline or 5% dextrose. Alternatively, a solution of the complex may be placed into an implant, such as an osmotic pump, for the slow release of the complex over an extended period of time. Alternatively, the complex may be provided in sustained release carrier formulations such as semi-permeable polymer carriers in the form of suppositories or microcapsules. See, for instance, U.S. Pat. No. 3,773,919 for Microcapsular Sustained Release Matrices Including Polylactides; Sidmon, et al. (1983) *Biopolymers* 22(1):547–556 for copolymers of L glutamic acid and gamma v-ethyl-L-glutamate; Langer, et al. (1981) *J. Biomed. Res.* 15:167–277 for poly(2-hydroxyethyl methacrylate) or the like.

The mode of administration delivers the complex to the individual in a safe, physiologically effective manner. The complex may be given by intranasal, subcutaneous, intravenous, intraperitoneal, or other conventional routes of administration. Preferably, the complex is injected subcutaneously, intravenously or intramuscularly. Most preferably, the complex is administered by subcutaneous injection. By subcutaneous injection, the complex appears not to be toxic or mitogenic at the injection site.

The dose of complex to be administered can be readily determined by those skilled in the art, based on the usual patient symptoms discussed above. Preferably, when the complex is administered to humans daily, the dosage of complex is at least about 0.05 mg IGF/kg of body weight/day, complexed to an equimolar amount of IGFBP-3. More preferably, the daily dosage of the complex for humans is at least 0.1 mg IGF/kg/day, complexed to an equimolar amount of IGFBP-3. If daily dosages in excess of about 0.5 mg IGF/kg must be given, the dosage may be divided and injected subcutaneously at two or more sites.

If the IGF/IGFBP-3 complex were administered to humans twice a week, each dose of complex is preferably at least about 0.1 mg IGF/kg of body weight, complexed to an equimolar amount of IGFBP-3. More preferably, for twice weekly administration, the dose of the complex is at least 0.5 mg IGF/kg, complexed to an equimolar amount of IGFBP-3. There is no known upper limit of dosage; however, it is preferable that a single dose not exceed 10 mg IGF/kg of body weight, when the IGF is complexed to an equimolar amount of IGFBP-3. These doses of IGF/IGFBP-3 complex are not expected to cause significant hypoglycemia since IGFBP-3 slows the IGF binding to cellular insulin receptors.

Preferably, the patient with renal disease is started with a relatively low dose of the complex, such as 0.05 mg IGF/kg of body weight/day, with an equimolar amount of IGFBP-3. The various factors given above should be monitored to determine if there is improvement. The patient should exhibit reduction in plasma creatinine, urea, proteinuria and the frequency of dialysis; and increases in GFR, RPF, urinary output and kidney size; reversal of tubular necrosis; and improvement in overall growth rate following such treatment. If the patient improves with the low dose, the low dose preferably should be continued until improvement in general health is achieved. Such an outcome may require several repetitions of therapy.

If the patient does not respond to low dose therapy with IGF and IGFBP-3 with sufficient reversal of the signs and symptoms of the nephropathy, the dose of complex should be increased gradually until such an outcome is achieved.

The invention has been disclosed by direct description. The following examples are intended to illustrate embodiments now known for practicing the invention, but the invention is not to be considered limited to these examples.

EXAMPLE 1

Comparison of IGF/IGFBP-3 Complex with IGF-I Alone

Groups of 10 male Sprague-Dawley rats were hypophysectomized (HYPOX) approximately 2 weeks prior to the initiation of the study and then were treated by subcutaneous injection with various doses of IGF-I, IGF-I/IGFBP-3 or the saline vehicle twice daily for 8 days. The dosages and treatment conditions utilized are listed below:

Group I: HYPOX—saline

Group IV: HYPOX—30 µg IGF-I

Group V: HYPOX—150 µg IGF-I

Group VIII: HYPOX—30 µg IGF-I+120 µg IGFBP-3

Group IX: HYPOX—150 µg IGF-I+600 µg IGFBP-3

Not shown are data from Groups II, III, VI and VII that were treated with growth hormone or IGFBP-3 alone and exhibited no relevant renal tissue effects.

The above dosages are stated in terms of total administration per rat/day and were delivered in two equal injection volumes of 0.2 ml each administered approximately 11 hours apart. The range of initial body weights for all groups of rats was 55.8–64.9 g. At the conclusion of the study, following collection of blood under anesthesia, the animals were sacrificed by cervical dislocation and selected organs were obtained for wet tissue weight determinations.

The FIGURE shows the effect of treatment with two doses of IGF-I/IGFBP-3 complex or equivalent doses of IGF-I alone on kidney weight as a percentage of total body weight. There was a statistically significant increase in the mean kidney weight as a percentage of total body weight compared to saline-treated controls produced by both 30 µg IGF-I alone and the combined 30 µg IGF-I+120 µg IGFBP-3 treatment. There was no dose response effect of increased free IGF-I on renal weight gain; however, half of the rats treated with 150 µg of free IGF-I died on this treatment. Although blood glucose concentrations were not measured, the cause of death was probably acute hypoglycemic shock, a well known consequence of bolus administration of this dosage of free IGF-I. All rats receiving an equivalent dosage of IGF-I with IGFBP-3 survived the study and demonstrated renal weight gain demonstrating the increased safety margin achieved by administration of IGF-I in complex with IGFBP-3. These findings in renal growth arrest in the hypophysectomy model demonstrate that in a situation of acute or chronic renal damage, higher doses of IGF-I can be safely administered with IGFBP-3 with an expectation of faster return of renal function.

EXAMPLE 2

Comparison of Effects of IGF/IGFBP-3 Complex With IGF-I Alone Renal Recovery

Adult Sprague-Dawley rats are anesthetized and the abdominal cavity is exposed by midline incision. Microvascular clamps are placed on both renal arteries to completely stop blood flow for 75 min. After this time, the clamps are removed and the kidneys are allowed to reperfuse before the incision is closed. Animals are divided into the following 5 treatment groups:

Group I: Ischemia—vehicle

Group II: Ischemia—150 µg IGF-I (bolus injection)

Group III: Ischemia—150 µg IGF-I (infusion)

Group IV: Ischemia—150 µg IGF-I+600 µg IGFBP-3

Group V: Ischemia—250 µg IGF-I+750 µg IGFBP-3

Treatment is initiated 30 minutes after surgery and is administered by subcutaneous injection once daily for 7 days in all groups except Group III. Group III animals are implanted subcutaneously with an Alzet mini-pump delivering IGF-I at a constant rate of 150 µg/day for the full course of the experiment. Animals are weighed daily for 7 days and tail vein blood is drawn both before the induction of tubular necrosis and daily thereafter for the measurement of glucose, hematocrit, serum creatinine, BUN and potassium. Measurements of renal function are performed on all rats on day 2 post-occlusion and initiation of therapy. Under anesthesia, left femoral arterial and venous catheters and a bladder catheter are inserted. Priming doses of inulin and PAH are administered in normal saline. Then a constant 40 µl/min infusion of inulin and PAH is initiated to maintain 50–100 mg/dl and 1–2 mg/dl plasma levels, respectively. After a 60 min. equilibration period, four consecutive 20 min. collections of urine and blood are performed for estimation of inulin and PAH levels as measured by standard techniques. Glomerular filtration rate (inulin clearance) and renal plasma flow (PAH clearance) are calculated and expressed as a percent of body weight.

Rats surviving to day 7 are sacrificed. Kidney wet weights are determined. Then kidneys are prepared for histopathologic examination. Sections are cut from formalin-fixed, paraffin-embedded kidneys and stained with hematoxylin/eosin and periodic acid/Schiff stains. A pathologic scoring system is used to grade the severity and extent of acute tubular necrosis typified by 1) epithelial calcification, 2) tubular dilatation and loss of brush border, 3) proximal tubular proliferation, and 4) interstitial infiltrate.

EXAMPLE 3

Treatment of End-Stage or Chronic Renal Failure

Pediatric and adult patients suffering from end-stage renal failure (ESRF) and chronic renal failure (CFR) due to a variety of causes (either on dialysis or with residual glomerular filtration) are separated into two groups. One group receives placebo, and one of which is treated by daily subcutaneous injection of IGF-I with its binding protein IGFBP-3. The dosage of IGF/IGFBP-3 ranges from 750 µg/kg/day to 2 mg/kg/day of IGF-I (with equimolar quantities of IGFBP-3) and is continued for from 7 to 130 days, or until a therapeutic effect is observed. Venous blood is obtained at baseline and during the course of treatment, and serum or plasma are stored at –20° C. until assayed. Twenty-four-hour urine collections are also obtained and stored similarly. Total serum IGF-I and free IGF are assessed by radioimmunoassay. Blood glucose levels and plasma levels of creatinine, urea and uric acid are determined by autoanalyzer. Albumin in urine is measured by an immunoturbidimetric method. Determination of renal size is determined by urogram at baseline and at the conclusion of the study.

This invention has been detailed both by example and by direct description. It should be apparent that one having ordinary skill in the art would be able to surmise equivalents to the invention as described in the claims which follow but which would be within the spirit of the description above. Those equivalents are to be included within the scope of this invention.

We claim:

1. A method of treating a renal disorder in a subject, said renal disorder selected from the group consisting of diabetic nephropathy and autoimmune nephropathy, said method comprising administering to said subject an effective amount of insulin-like growth factor (IGF) and insulin like growth factor binding protein 3 (IGFBP-3).

2. The method of claim 1 wherein said treatment results in an increase in kidney mass in said subject.

3. The method of claim 1 wherein the IGF-I and IGFBP-3 are administered subcutaneously, intravenously, intramuscularly, or by implanted device.

4. The method of claim 1 wherein the IGF is administered subcutaneously at a dose of about 0.05 mg of IGF per kilogram of body weight per day, said IGF administered as an approximately equimolar mixture with IGFBP-3.

5. The method of claim 1 wherein said subject is selected from humans, mammalian farm animals, sport animals and pets.

6. The method of claim 1 wherein the IGF is obtained from natural sources or prepared by recombinant or chemical means.

7. The method of claim 1 wherein the IGFBP-3 is obtained from natural sources or prepared by recombinant or chemical means.

8. The method of claim 1 wherein said IGF is IGF-I.

9. The method of claim 1 wherein said IGF is IGF-II.

10. The method of claim 8 wherein said IGF-I and IGFBP-3 are administered as a preformed complex.

11. The method of claim 1 wherein said renal disorder is diabetic nephropathy.

12. The method of claim 2 wherein said renal disorder is diabetic nephropathy.

13. The method of claim 1 wherein said renal disorder is autoimmune nephropathy.

14. The method of claim 2 wherein said renal disorder is autoimmune nephropathy.

15. The method of 3 wherein said renal disorder is diabetic nephropathy.

16. The method of claim 3 wherein said renal disorder is autoimmune nephropathy.

17. The method of claim 15 wherein said preformed complex of IGF-I and IGFBP-3 is at least about 0.05 mg of IGF-I per kilogram of body weight per day, complexed to an equimolar amount of IGFBP-3.

18. The method of claim 16 wherein said preformed complex of IGF-I and IGFBP-3 is at least about 0.05 mg of IGF-I per kilogram of body weight per day, complexed to an equimolar amount of IGFBP-3.

* * * * *